United States Patent [19]
Kamataki

[11] Patent Number: 5,447,719
[45] Date of Patent: Sep. 5, 1995

[54] β-GLUCURONIDASE INHIBITOR
[75] Inventor: Tetsuya Kamataki, Sapporo, Japan
[73] Assignee: Tsumura & Co., Tokyo, Japan
[21] Appl. No.: 30,346
[22] PCT Filed: Aug. 3, 1992
[86] PCT No.: PCT/JP92/00988
  § 371 Date: Mar. 25, 1993
  § 102(e) Date: Mar. 25, 1993
[87] PCT Pub. No.: WO93/02684
  PCT Pub. Date: Feb. 18, 1993
[30] Foreign Application Priority Data
  Aug. 9, 1991 [JP] Japan .................. 3-223665
[51] Int. Cl.[6] .................. A61K 35/78; A61K 31/70
[52] U.S. Cl. .................. 424/195.1; 514/25; 514/456; 424/451; 424/464
[58] Field of Search .................. 536/8; 514/25, 456; 435/184; 424/195.1, 451, 464

[56] References Cited
PUBLICATIONS

Yoshiyuki Kimura et al, "Effects of Baicalein on Leukotriene Biosynthesis and Degranulation in Human Polymorphonuclear Leukocytes", *Biochimica et Biophysica Acta*, vol. 922, No. 3, pp. 278–286 (1987).
E. Middleton et al, "The Effects of Citrus Flavonoids on Human Basophil and Neutrophil Function", *Planta Medica*, vol. 53, No. 4, pp. 325–328 (1987).
M. Narita et al, "Inhibition of Beta-Glucuronidase by Natural Glucuronides of Kampo Medicines Using Glucuronide of SN-38 (7-ethyl-10-hydroxycamptothecin) as Substrate", *Xenobiotica*, vol. 23, No. 1, pp. 5–10 (1993).
Masaru Kawasalo et al, "8-Hydroxytricetin 7—Glucuronidase Inhibitor from Scoparia Dulcis", *Phytochemistry*, vol. 27, No. 11, pp. 3709–3711 (1988). Abstract.
W. Suzuki et al, "Studies of the Metabolic Fate of CPT-11(2): Pharmacokinetics in Rats Following a Single Intravenous Dose (2)—Metabolites Pattern in Serum, liver, Kidney and Intestinal Tissue", *Xenobiotic Metabolism and Disposition*, vol. 6, No. 1, pp. 97–104 (1991).
L. M. Ball et al, "Formation of Mutagenic Urinary Metabolites from 1-Nitropyrene in Germ-Free and Conventional Rats: Role of the Gut Flora", *Carcinogenesis*, vol. 12, No. 1, pp. 1–5 (1991).
The Merck Index, 11th edition, published 1989, pp. 150–151, Compound No. 954.
Y. Takino et al, *Chemical and Pharmaceutical Bulletin*, vol. 35, No. 8, pp. 3494–3497 (1987) "Determination of Some Flavonoids in Scutellariae Radix by High-performance Liquid Chromatography".
Xian Fany Liu et al, *Molecular Oncology*, vol. 37, No. 6, pp. 911–915 (1990), "Inhibition of rat Liver NAD(p)H".

*Primary Examiner*—John W. Rollins
*Attorney, Agent, or Firm*—Burns, Doane, Swecker & Mathis

[57] ABSTRACT

A β-glucuronidase inhibitor comprising at least one compound selected from the group consisting of baicalin, oroxylin A-7-O-glucuronide and luteolin-3'-glucuronide; an extract of scutellaria root (baikal skullcap; *Scutellariae Radix*) and/or schizonepeta spike (Japanese catnip; *Schizonepelae Spica*); or a Chinese and Japanese traditional prescription comprised of scutellaria root (baikal skullcap; *Scutellariae Radix*) and/or schizonepeta spike (Japanese catnip; *Schizonepelae Spica*) as a crude drug. The β-glucuronidase inhibitor can relieve the adverse effect, especially diarrhea, caused in the administration of a compound represented by the following formula I

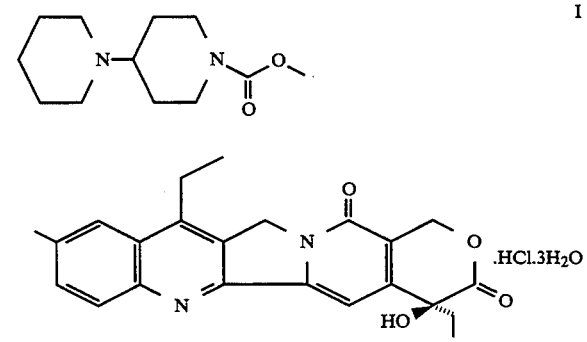

12 Claims, No Drawings 5,447,719

β-GLUCURONIDASE INHIBITOR

TECHNICAL FIELD

The present invention relates to a β-glucuronidase inhibitor which inhibits β-glucuronidase and is useful in the field of medicine.

BACKGROUND ART

Camptothecin is a kind of a plant alkaloid contained in "Kiju" (Camptotheca acuminate Decne.) native to China, and the like. Although the development thereof was advanced as an antitumor agent, it was suspended due to toxicity thereof such as strong inhibition of bone marrow. Thereafter, the camptothecin was used as a starting material and subjected to various chemical modifications to synthesize a compound represented by the following formula I and having a high antitumor activity and a wide range of an antitumor spectrum (see Japanese Examined Patent Publication (Kokoku) No. 3-4077).

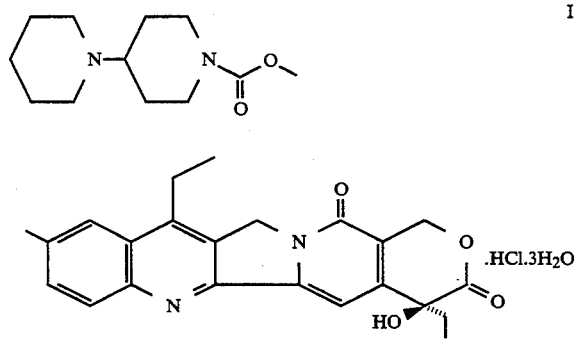

However, the compound represented by the formula I was found to cause diarrhea as an adverse effect when it was clinically applied. The substance causative of the diarrhea has been estimated to be a compound (7-ethyl-10-hydroxycamptothecin) represented by the following formula III

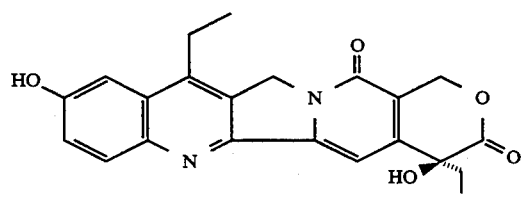

which is produced when a glucuronic acid inclusion compound (7-ethylcamptothecin-10-yl β-D-glucopyranosidouronic acid) which is a main metabolite of the compound represented by the formula I and represented by the formula II is subjected to the action of β-glucuronidase in an alimentary canal.

For this reason, it is expected that the prevention of the elimination of glucuronic acid through the inhibition of the enzymatic activity of β-glucuronidase in the alimentary canal enables the formation of the compound represented by the formula III to be prevented, so that the occurrence of diarrhea can be suppressed.

DISCLOSURE OF THE INVENTION

Accordingly, an object of the present invention is to develop a β-glucuronidase inhibitor excellent in the effect of relieving the adverse effect, especially diarrhea, caused in the administration of the compound represented by the formula I.

The present inventors have made extensive and intensive studies with a view to solving the above-described problem and, as a result, have found a Chinese and Japanese traditional prescription, a crude drug and a compound contained in the crude drug each having a capability of inhibiting the enzymatic activity of β-glucuronidase, which has led to the completion of the present invention.

Specifically, the present invention provides a β-glucuronidase inhibitor comprising at least one compound selected from the group consisting of baicalin, oroxylin A-7-O-glucuronide and luteolin-3'-glucuronide (these three compounds being hereinafter collectively referred to as "active ingredient compound of the present invention"); an extract of scutellaria root (baikal skullcap; *Scutellariae Radix*) and/or schizonepeta spike (Japanese catnip; *Schizonepelae Spica*); or a Chinese and Japanese traditional prescription comprised of scutellaria root (baikal skullcap; *Scutellariae Radix*) and/or schizonepeta spike (Japanese catnip; *Schizonepelae Spica*) as a crude drug.

BEST MODE FOR CARRYING OUT THE INVENTION

Baicalin is known as an ingredient contained in scutellaria root (baikal skullcap; *Scutellariae Radix*) (see Chuyaku Daijiten published by Shanhai Kagaku Gijutsu Shuppansha and edited by Shogakukan Inc.). Baicalin useable in the present invention may be commercially available from Wako Pure Chemical Industries, Ltd. Further, it can be easily produced by a method described in "Yakkyoku", vol. 13, No. 8, 53–55 (1962) or Acta Phytochim., 5, 219 (1931), and baicalin thus produced may also be used in the present invention.

Oroxylin A-7-O-glucuronide and luteolin-3'-glucuronide can be produced respectively from scutellaria root (baikal skullcap; *Scutellariae Radix*) and schizonepeta spike (Japanese catnip; *Schizonepelae Spica*) as follows.

Scutellaria root (baikal skullcap; *Scutellariae Radix*) or schizonepeta spike (Japanese catnip; *Schizonepelae Spica*) is extracted with water, an alcohol, a mixed sol-

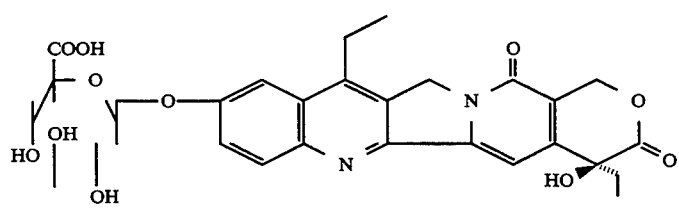

vent comprising water and an alcohol or a mixed solvent comprising water and acetone. The solvent is removed from the extract, and the residue is subjected to the following chromatography as it is or optionally after it is dissolved in water, an alcohol, a mixed solvent comprising water and an alcohol or a mixed solvent comprising water and acetone, the solution is extracted with an organic solvent, such as petroleum ether, an ether or chloroform, and the fat soluble ingredient transferred to the resultant organic solvent phase is removed. The chromatography is repeated several times by column chromatography using as a carrier a porous polymer, such as Diaion HP-20 or MCI gel CHP20P, sephadex, such as Sephadex LH-20, reversed phase silica gel, silica gel, polyamide, activated carbon or cellulose and high performance liquid chromatography with at least one member selected from water, methanol, ethanol, acetic acid, chloroform, ethyl acetate, n-hexane, acetone and benzene being used as an eluent, and fractionation is conducted by thin-layer chromatography while confirming the intended ingredient. If necessary, purification may be conducted by recrystallization from a suitable solvent, such as methanol or ethanol.

Specific examples of the production of oroxylin A-7-O-glucuronide and luteolin-3'-glucuronide will now be described.

EXAMPLE 1

Scutellaria root (Baikal Skullcap; *Scutellariae Radix*) was extracted with methanol, and the solvent was removed by distillation. The extract was suspended in water, and the suspension was extracted with butanol. The extract was applied to Sephadex LH-20 column chromatography and developed with water-methanol (6:1 to 1:2) to obtain a fraction containing oroxylin A-7-O-glucuronide. This fraction was further applied to silica gel column chromatography and developed with chloroform-water-formic acid (100:15:2:0.5) to provide oroxylin A-7-O-glucuronide.

EXAMPLE 2

9.9 kg of a spike of schizonepeta spike (Japanese catnip; *Schizonepelae Spica*) was extracted with 36 liters of methanol, and the solvent was removed from the resultant extract to provide a methanol extract. The methanol extract was dissolved in water/methanol. The solution was extracted with chloroform. The resultant fat soluble ingredient was removed, and the residue was applied to Diaion HP-20 (manufactured by Mitsubishi Kasei Corp.) column chromatography, and elution was conducted with 6 liters of water, 50% methanol/water (10 liters) and then 10 liters of 100% methanol.

The solvent contained in a fraction eluted with 50% methanol/water and the solvent contained in a fraction eluted with 100% methanol were removed by distillation under reduced pressure to provide 78.2 g of a fraction eluted with 50% methanol/water and 50.5 g of a fraction eluted with 100% methanol.

50.5 g of the fraction eluted with 100% methanol was applied to Diaion HP-20 (manufactured by Mitsubishi Kasei Corp.) column chromatography, and the fraction eluted with 100% methanol was applied to Sephadex LH-20 (manufactured by Pharmacia Fine Chemical) column chromatography. In this case, water was used as the first eluent, and the ethanol content of the eluent was then gradually increased to provide 2.4 g of a fraction eluted with 25% aqueous ethanol/water, 6.9 g of a fraction eluted with 50% ethanol/water, 6.7 g of a fraction eluted with 75% ethanol/water and 3.7 g of a fraction eluted with 100% ethanol. These fractions were subjected to column chromatography using MCI gel HP20P comprising a porous polymer (manufactured by Mitsubishi Kasei Corp.). In this case, water was used as the first eluent, and the ethanol content of the eluent was then gradually increased to provide fractions A and B from the fraction eluted with 25% methanol/water and a fraction C from the fraction eluted with 50% methanol/water.

The fraction C was further subjected to high performance liquid chromatography (a packed column for partition adsorption chromatography TSKgel ODS-80TM manufactured by Tosoh Corporation), and elution was effected with 45% methanol/water to provide 93 mg of luteolin-3'-glucuronide as a pale yellow amorphous powder.

The extract of scutellaria root (baikal skullcap; *Scutellariae Radix*) and/or schizonepeta spike (Japanese catnip; *Schizonepelae Spica*) can be obtained by extracting scutellaria root (baikal skullcap; *Scutellariae Radix*) and/or schizonepeta spike (Japanese catnip; *Schizonepelae Spica*) with water or an organic solvent at room temperature or under heating conditions, filtering the resultant extract and drying the filtrate by conventional drying means such as spray drying, lyophilization or evaporation to dryness. The resultant extract, as such, may be used. Alternatively, excipients, auxiliary agents, etc., used in conventional preparations may be added to the extract followed by preparation of powders, granules, tablets, capsules, etc., according to a conventional method for producing preparations.

Specific examples of the production of the extract of scutellaria root (baikal skullcap; *Scutellariae Radix*) and/or schizonepeta spike (Japanese catnip; *Schizonepelae Spica*) will now be described.

EXAMPLE 3

150 ml of water was added to 15 g of scutellaria root (baikal skullcap; *Scutellariae Radix*), and extraction was conducted at 100° C. for one hour. The resultant extract was filtered, and the filtrate was evaporated to dryness to provide 1.8 g of a dried extract.

EXAMPLE 4

150 ml of water was added to 15 g of schizonepeta spike (Japanese catnip; *Schizonepelae Spica*), and extraction was conducted at 100° C. for one hour. The resultant extract was filtered, and the filtrate was evaporated to dryness to provide 1.6 g of a dried extract.

Specific examples of the Chinese and Japanese traditional prescription comprised of scutellaria root (baikal skullcap; *Scutellariae Radix*) and/or schizonepeta spike (Japanese catnip; *Schizonepelae Spica*) as a crude drug include Otuzi-to (Yi-Zi-Tang), Zyumi-haidoku-to (Shi-Wei-Bai-Du-Tang), Dai-saiko-to (Da-Chai-Hu-Tang), Sho-saiko-to (Xiao-Chai-Hu-Tang), Saiko-keisi-to (Chai-Hu-Gui-Zhi-Tang), Saiko-keishi-kankyo-to (Chai-Hu-Gui-Zhi-Gan-Jiang-Tang), Saiko-ka-ryukotu-borei-to (Chai-Hu-Jia-Long-Gu-Mu-Li-Tang), Hange-syasin- to (Ban-Xia-Xie-Xin-Tang), Oren-gedoku-to (Huang-Lian-Jie-Du-Tang), Boi-ogi-to (Fang-Yi-Huang-Qi-Tang), Syohu-san (Xiao-Feng-San), Keigai-rengyo-to (Jing-Jie-Lian-Qiao-Tang), Zyuntyo-to (Run-Chang-Tang), Gorin-san (Wu-Lin-San), Unsei-in (Wen-Qing-Yin), Sei-zyo-bohu-to (Qing-Shang-Fang-Feng-Tang), Bohu-tusyo-san (Fang-Feng-Tong-Sheng- San), Nyoshin-san (Nu-Shen-San), Kanbaku-taiso-to (Gan-Mai-Da-Zao-Tang), Ryutan-syakan-to (Long-Dan-Xie-Gan-Tang), Zhi-zuso-ippo, (Zhi-Tou-Chuang-Yi-Fang), Toki-insi (Dang-Gui-Yin-Zi), Senkyu-tyatyo- san (Chuan-Xiong-Cha-Tiao-San), Saiko-sei-kan-to (Chai-Hu-Qing-Gan-Tang), Nizyutu-to (Er-Shu-Tang), Seihai-to (Qing-Fei-Tang), Saiboku-to (Chai-Pu-Tang), Sin'i-seihai-to (Xin-Yi-Qing-Fei-Tang), Syo-saiko-to-ka-kikyo-sekko (Xiao-Chai-Hu-Tang-Jia-Jie-Geng-Shi-Gao), Seisin-rensi-in (Qing-Xin-Lian-Zi-Yin), San'o-syasin-to (San-Huang-Xie-Xin-Tang), Sairei-to (Chai-Ling-Tang) and Sammotu-ogon-to (San-Wu-Huang-Qin-Tang). These Chinese and Japanese traditional prescriptions may be produced by conventional methods, for example, as described in a guideline for general Chinese and Japanese traditional prescriptions (complied under the supervision of the Pharmaceutical Affairs Bureau of Ministry of Health and Welfare). As with the above-described extracts, these Chinese and Japanese traditional prescriptions may be used as they are or in the form of preparations.

Specific examples of the production of the Chinese and Japanese traditional prescription comprising scutellaria root (baikal skullcap; *Scutellariae Radix*) and/or schizonepeta spike (Japanese catnip; *Schizonepelae Spica*) as a crude drug will now be described.

EXAMPLE 5

Purified water was added to 7 g of bupleurum root (*Bupleuri Radix*), 5 g of pinellia tuber (*Pinelliae Tuber*), 1 g of ginger rhizome (*Zingiberis Rhizoma*), 3 g of scutellaria root (baikal skullcap; *Scutellariae Radix*), 3 g of jujube fruit (*Zizyphi Fructus*), 3 g of ginseng root (*Ginseng Radix*) and 2 g of glycyrrhiza root (*glycyrrhizae radix*) in such a manner that the amount of the purified water was 30 times that of the crude drug. The mixture was extracted at 100° C. for 60 min, and solid-liquid separation was conducted. The separated solution was concentrated until the volume was halved. The concentrate was spray dried to provide a dried extract powder of Sho-saiko-to (Xiao-Chai-Hu-Tang).

EXAMPLE 6

Purified water was added to 7 g of bupleurum root (*Bupleuri Radix*), 5 g of pinellia tuber (*Pinelliae Tuber*), 5 g of hoelen (*hoelen*), 3 g of scutellaria root (baikal skullcap; *Scutellariae Radix*), 3 g of magnolia bark (*Magnoliae Corlex*), 3 g of jujube fruit (*Zizyphi Fructus*), 3 g of ginseng root (*Ginseng Radix*), 2 g of glycyrrhiza root (*glycyrrhizae radix*), 2 g of perilla herb (*Perillae Herba*) and 1 g of ginger rhizome (*Zingiberis Rhizoma*) in such a manner that the amount of the purified water was 28 times that of the crude drug. The mixture was extracted at 100° C. for 60 min, and solid-liquid separation was conducted. The separated solution was concentrated until the volume was halved. The concentrated was spray dried to provide a dried extract powder of Saiboku-to (Chai-Pu-Tang).

EXAMPLE 7

Purified water was added to 7 g of bupleurum root (*Bupleuri Radix*), 5 g of alisma rhizome (*alismalis Rhizoma*), 5 g of pinellia tuber (*Pinellia Tuber*), 33 g of scutellaria root (baikal skullcap; *Scutellariae Radix*), 3 g of atractylodes lancea rhizome (*Atractylodis Lanceae Rhizoma*), 3 g of jujube fruit (*Zizyphi Fructus*), chuling (Polyporus), 3 g of ginseng root (*Ginseng Radix*), 3 g of hoelen (*hoelen*), 2 g of glycyrrhiza root (*Glycyrrhizae Radix*), 2 g of cinnamon bark (*Cinnamomi Cortex*) and 1 g of ginger rhizome (*Zingiberis Rhizoma*) in such a manner that the amount of the purified water was 40 times that of the crude drug. The mixture was extracted at 100° C. for 60 min, and solid-liquid separation was conducted. The separated solution was concentrated until the volume was halved. The concentrate was spray dried to provide a dried extract powder of Sairei-to (Chai-Ling-Tang).

The $\beta$-glucuronidase inhibitory activity of the active ingredient of the present invention will now be described with reference to the following Experiment Examples.

EXPERIMENT EXAMPLE 1

$\beta$-glucuronidase (manufactured by Sigma Chemical Co.) derived from *Escherichia coli* was added to a reaction solution comprising 50 $\mu$l of potassium phosphate buffer (pH: 6.8), a solution of a compound (100 nmol/ml) represented by the formula II and produced by Reference Example which will be described later and a specimen, and a reaction was allowed to proceed at 37° C. for 20 min. A glycine buffer (pH: 10.4) was added to terminate the reaction. 10 $\mu$l of the reaction mixture and 100 $\mu$l of an internal standard (camptothecin) solution were added to 1 ml of a 0.01N aqueous hydrochloric acid solution, and the mixture was applied to Bond Elute $C_{18}$ (Analytichem), washed with water and 0.01N aqueous hydrochloric acid solution. Elution was effected with acetonitrile/water (1:2). 100 $\mu$l of the eluate obtained by elution with acetonitrile/water (1:2) was analyzed by high performance liquid chromatography (HPLC) under the following conditions, and the $\beta$-glucuronidase activity was calculated by using the amount of production of the compound represented by the formula III as an indication. The residual activity (%) in each concentration of the specimen is given in Table 1.

Conditions

Apparatus: high performance liquid chromatograph HLC-803D manufactured by Toyo Soda Analytical column: Tosoh ODS-80TM 250×4.6 mm (I.D.)

Thermostatic chamber of column: Tosoh CO-8011 40° C.

Guard column: Tosoh TSKguradgel ODS-120T

Detector: Shimazu Fluorescence HPLCMonitor RF-530

Detection wavelength: Ex380nm Em556nm

Autosampler: Tosoh AS-8000

Eluent: acetonitrile/water (1:2)

Flow rate: 1.0 ml/min

TABLE 1

| Specimen | Residual Activity (%) | | | |
|---|---|---|---|---|
|  | 3.0 nM | 16.7 nM | 33.3 nM | 166.7 nM |
| Baicalin | 58.0 | 19.0 | 10.7 | 2.3 |
| Oroxylin A-7-O-glucuronide | 42.5 | 31.1 | 17.0 | 3.0 |
| Luteolin-3'-glucuronide | 67.7 | 28.5 | 13.2 | 2.1 |

The results of Experiment Example 1 demonstrate that the active ingredient compounds of the present invention are useful as the $\beta$-glucuronidase inhibitor.

The $\beta$-glucuronidase inhibitor of the present invention can inhibit the adverse effect caused in the administration of the compound represented by the formula 1, especially the occurrence of diarrhea. This eliminates the limitation on the administration of the compound represented by the formula 1 to patients suffering from cancers, which can greatly contribute to the treatment of cancers.

The dose and formulation of the β-glucuronidase of the present invention will now be described.

The compound of the present invention can be administered in itself or together with a general preparation carrier to animals and human being. The dosage form is not particularly limited and can be properly selected according to need. Examples of the dosage form include oral preparations such as tablets, capsules, granules, fine subtilaes and powders and parenteral preparations such as injections and suppositories.

In order to exhibit the intended effect as an oral preparation, it would be generally suitable that the compound of the present invention is dividedly administered several times at a dose of 10 mg to 1 g per day per adult in terms of the weight of the active ingredient compound of the present invention, 1 to 10 g per day per adult in terms of the dry weight of an extract of scutellaria root (baikal skullcap) and/or schizonepeta spike (Japanese catnip) and 1 to 10 g per day per adult in terms of the dry weight of an extract powder according to Chinese medicine formulation although the dose varies depending upon the age, weight and severity of disease of the patient.

The oral preparations are produced according to a conventional method through the use of excipients, for example, starch, lactose, saccharose, mannite, carboxymethyl cellulose, corn starch or an inorganic salt.

In the preparations of this type, binders, disintegrators, surfactants, lubricants, fluidity accelerators, corrigents, colorants, perfumes, etc., may be properly used besides the above-described excipients. Specific examples of these additives will now be described.

Binder

Starch, dextrin, gum arabic, gelatin, hydroxypropyl starch, methyl cellulose, sodium carboxymethyl cellulose, hydroxypropyl cellulose, crystalline cellulose, ethyl cellulose, polyvinyl pyrrolidone and macrogol.

Disintegrator

Starch, hydroxypropylstarch, sodium carboxymethyl cellulose, calcium carboxymethyl cellulose, carboxymethyl cellulose and lowly substituted hydroxypropyl cellulose.

Surfactant

Sodium laurylsulfate, soybean lecithin, sucrose fatty acid ester and polysorbate 80.

Lubricant

Talc, wax, hydrogenated vegetable oil, sucrose fatty acid ester, magnesium stearate, calcium stearate, aluminum stearate and polyethylene glycol.

Fluidity accelerator

Precipitated silicic acid anhydride, dried aluminum hydroxide gel, synthetic aluminum silicate and magnesium silicate.

Further, the compound of the present invention can be administered also in the form of a suspension, an emulsion, a syrup or an alixir. These various dosage forms may contain corrigents, stabilizers and colorants.

In order to attain the intended effect when the compound of the present invention is administered in the form of a parenteral preparation, it would be generally suitable that the compound of the present invention is administered through intravenous injection, intravenous drip, subcutaneous injection or intramuscular injection at a dose of 0.1 to 5 mg per day per adult although the dose varies depending upon the age, weight and severity of disease of the patient.

The parenteral agent can be produced according to a conventional method. In this case, distilled water for injection, physiological saline, aqueous glucose solution, vegetable oil for injection, sesame oil, peanut oil, soybean oil, corn oil, propylene glycol, polyethylene glycol, etc., may be generally used as a diluent. Further, if necessary, germicides, preservatives and stabilizers may be added. From the viewpoint of stability, the parenteral preparation may be used as follows. Specifically, the parenteral preparation is filled into a vial and frozen, water is removed by a conventional lyophilization technique, and a solution is prepared again from the lyophilized preparation immediately before use. Further, if necessary, it is also possible to properly add tonicity agents, stabilizers, preservatives, soothing agents, etc.

Examples of other parenteral preparation include liquids for external use, liniments such as ointments and suppositories for intrarectal administration. These may be produced by a conventional method.

Examples of preparations wherein use is made of the compound of the present invention will now be described.

PREPARATION EXAMPLE 1

| | | |
|---|---|---|
| ① Corn starch | | 44 g |
| ② Crystalline cellulose | | 40 g |
| ③ Calcium carboxymethyl cellulose | | 5 g |
| ④ Precipitated silicic acid anhydride | | 0.5 g |
| ⑤ Magnesium stearate | | 0.5 g |
| ⑥ Baicalin | | 10 g |
| | Total | 100 g |

According to the above-described formulation, the components ① to ⑥ were homogeneously mixed with each other, and the mixture was compression-molded by means of a tableting machine into tablets having a weight of 200 mg per tablet.

The tablet contained baicalin in an amount of 200 g per tablet. It is dividedly administered several times at a dose of 3 to 10 tablets per day per adult.

PREPARATION EXAMPLE 2

| | | |
|---|---|---|
| ① Crystalline cellulose | | 84.5 g |
| ② Magnesium stearate | | 0.5 g |
| ③ Calcium carboxymethyl cellulose | | 5 g |
| ④ Oroxylin A-7-O-glucuronide | | 10 g |
| | Total | 100 g |

According to the above-described formulation, the components ① and ④ and part of the component ② were homogeneously mixed with each other, and the mixture was subjected to compression molding and pulverized. The component ③ and the remaining amount of the component ② were added and mixed therewith. The mixture was compression-molded by means of a tableting machine into tablets having a weight of 200 mg per tablet.

The tablet contained oroxylin A-7-O-glucuronide in an amount of 20 mg per tablet. It is dividedly administered several times at a dose of 3 to 10 tablets per day per adult.

PREPARATION EXAMPLE 3

| | | |
|---|---|---|
| ① Crystalline cellulose | 34.5 g | |
| ② 10% Hydroxypropyl cellulose ethanol solution | 50 g | |
| ③ Calcium carboxymethyl cellulose | 5 g | |
| ④ Magnesium stearate | 0.5 g | |
| ⑤ Luteolin-3'-glucuronide | 10 g | |
| | Total | 100 g |

According to the above-described formulation, the components ①, ② and ⑤ were homogeneously mixed with each other, and the mixture was kneaded by a conventional method and granulated by means of an extruding granulator. The granules were dried and crushed, and the components ③ and ④ were mixed therewith. The mixture was compression-molded by means of a tableting machine into tablets having a weight of 200 mg per tablet.

The tablet contained luteolin-3'-glucuronide in an amount of 20 mg per tablet. It is dividedly administered several times at a dose of 3 to 10 tablets per day per adult.

PREPARATION EXAMPLE 4

| | | |
|---|---|---|
| ① Corn starch | 84 g | |
| ② Magnesium stearate | 0.5 g | |
| ③ Calcium carboxymethyl cellulose | 5 g | |
| ④ Precipitated silicic acid anhydride | 0.5 g | |
| ⑤ Baicalin | 10 g | |
| | Total | 100 g |

According to the above-described formulation, the components ① to ⑤ were homogeneously mixed with each other, and the mixture was subjected to compression molding by means of a compression molding machine, pulverized by means of a pulverizer and sieved to give a granule.

1 g of the granules contained 100 mg of baicalin. It is dividedly administered several times at a dose of 0.6 to 2 g per day per adult.

PREPARATION EXAMPLE 5

| | | |
|---|---|---|
| ① Crystalline cellulose | 55 g | |
| ② 10% Hydroxypropyl cellulose ethanol solution | 35 g | |
| ③ Oroxylin A-7-O-glucuronide | 10 g | |
| | Total | 100 g |

According to the above-described formulation, the components ① to ③ were homogeneously mixed with each other, and the mixture was subjected to kneading and granulated by means of an extruding granulator. The granule was cried and sieved to give a granule preparation.

1 g of the granule contained 100 mg of oroxylin A-7-O-glucuronide. It is dividedly administered several times at a dose of 0.6 to 2 g per day per adult.

PREPARATION EXAMPLE 6

| | | |
|---|---|---|
| ① Corn starch | 89.5 g | |
| ② Precipitated silicic acid anhydride | 0.5 g | |
| ③ Luteolin-3'-glucuronide | 10 g | |
| | Total | 100 g |

According to the above-described formulation, the components ① to ③ were homogeneously mixed with each other, and 200 mg of the mixture was filled into a No. 2 capsule.

The capsule contained 20 mg of luteolin-3'-glucuronide per capsule. It is dividedly administered several times at a dose of 3 to 10 capsules per day per adult.

PREPARATION EXAMPLE 7

| | | |
|---|---|---|
| ① Distilled water for injection | 89.5 g | |
| ② Soybean oil | 5 g | |
| ③ Soybean phospholipid | 2.5 g | |
| ④ Glycerin | 2 g | |
| ⑤ Baicalin | 1 g | |
| | Total amount | 100 g |

According to the above formulation, the component ⑤ was dissolved in ② and ③, and a solution comprising ① and ④ was added thereto for emulsification, thereby providing an injection.

PREPARATION EXAMPLE 8

| | | |
|---|---|---|
| ① Crystalline cellulose | 33.5 g | |
| ② Magnesium stearate | 0.5 g | |
| ③ Oroxyline A-7-O-glucuronide | 66 g | |
| | Total | 100 g |

According to the above-described formulation, the components ① to ③ were homogeneously mixed with each other, and the mixture was compression-molded, crushed by means of a crusher and sieved to provide a granule preparation.

1 g of the granules contained 660 mg of oroxylin A-7-O-glucuronide. It is dividedly administered several times at a dose of 0.09 to 0.3 g per day per adult.

PREPARATION EXAMPLE 9

| | | |
|---|---|---|
| ① Crystalline cellulose | 10 g | |
| ② Magnesium stearate | 0.5 g | |
| ③ Luteolin-3'-glucuronide | 89.5 g | |
| | Total | 100 g |

According to the above-described formulation, the components ① to ③ were homogeneously mixed with each other, and the mixture was compression-molded, crushed by means of a crusher and sieved to provide a granule preparation.

1 g of the granules contained 895 mg of luteolin-3'-glucuronide. It is dividedly administered several times at a dose of 0.07 to 0.22 g per day per adult.

Reference Example of the production of the compound represented by the above-described formula II used in the Experiment Examples will now be described.

REFERENCE EXAMPLE

A naturally occurring camptothecin as a starting compound was subjected to a radical alkylation reaction and a reaction through N-oxide (as disclosed in Japanese Unexamined Patent Publication (Kokai) No.

56-158786 and Japanese Unexamined Patent Publication (Kokai) No. 58-39683) to produce a compound represented by the formula III which is then reacted with a halogen derivative of glucuronic acid and subjected to deblocking to provide a compound represented by the formula II (as disclosed in Japanese Unexamined Patent Publication (Kokai) No. 63-238098).

I claim:

1. A method of inhibiting $\beta$-glucuronidase activity in a patient, comprising administering to a patient in need of such inhibition, an effective amount for inhibiting $\beta$-glucuronidase activity of at least one extract selected from the group consisting of extracts of scutellaria root (baikal skullcap; *Scutellariae Radix*) and schizonepeta spike (Japanese catnip; *Schizonepelae Spica*).

2. A method according to claim 1, wherein the extracts of scutellaria root (baikal skullcap: *Scutellariae Radix*) and schizonepeta spike (Japanese catnip; *Schizonepelae Spica*) comprise at least one compound selected from the group consisting of baicalin, oroxylin A-7-O-glucuronide and luteolin-3'-glucuronide.

3. A method according to claim 1, wherein the extracts are administered in the form of a Chinese and Japanese traditional prescription which comprises at least one extract selected from the group consisting of scutellaria root (baikal skullcap; *Scutellariae Radix*) and schizonepeta spike (Japanese catnip; *Schizonepelae Spica*).

4. A method according to claim 1 wherein the extracts are administered to the patient by an oral or parenteral dosage form.

5. A method according to claim 4 wherein the oral dosage form is selected from tablets, capsules, granules, fine subtilaes or powders.

6. A method according to claim 5 wherein the oral dosage form further comprises at least one excipient, binder, disintegrator, surfactant, lubricant, fluidity accelerator, corrigent, colorant, or perfume.

7. A method according to claim 4 wherein the oral dosage form is administered to the patient at a dose of 10 mg to 1 g per day by weight of the extract.

8. A method according to claim 4 wherein the parenteral dosage form is selected from an injection or a suppository.

9. A method according to claim 8 wherein the parenteral dosage form is selected from intravenous injection, subcutaneous injection or intramuscular injection.

10. A method according to claim 4 wherein the parenteral dosage form is administered to the patient at a dose of 0.1 to 5 mg per day by weight of the extract.

11. A method according to claim 4 wherein the parenteral dosage form is intravenous drip.

12. A method according to claim 1 wherein the extracts are administered in a dosage form selected from suspension, emulsion, syrup or elixir.

* * * * *